United States Patent [19]

Augustsson

[11] Patent Number: 4,798,961
[45] Date of Patent: Jan. 17, 1989

[54] DEVICE FOR RADIATION FIELD SHIELDING IN RADIOTHERAPY

[76] Inventor: Nils-Erik Augustsson, Fasanvägen 2, S-232 00 Åkarp, Sweden

[21] Appl. No.: 81,006
[22] PCT Filed: Nov. 11, 1986
[86] PCT No.: PCT/SE86/00514
  § 371 Date: Jul. 9, 1987
  § 102(e) Date: Jul. 9, 1987
[87] PCT Pub. No.: WO87/02897
  PCT Pub. Date: May 21, 1987

[30] Foreign Application Priority Data
  Nov. 11, 1985 [SE] Sweden ................................ 8505315

[51] Int. Cl.$^4$ ............................................. H05G 1/02
[52] U.S. Cl. .................................... 250/515.1; 378/65; 378/145
[58] Field of Search ............... 250/515.1; 378/65, 145, 378/203, 210

[56] References Cited

U.S. PATENT DOCUMENTS

| | | | |
|---|---|---|---|
| 3,723,743 | 3/1973 | Brackenbrough et al. | 250/515.1 |
| 3,982,133 | 9/1976 | Jupa et al. | 250/505.1 |
| 4,027,167 | 5/1977 | Pollermann | 250/515.1 |
| 4,158,779 | 6/1979 | Rommel et al. | 250/515.1 |
| 4,214,167 | 7/1980 | Gade | 250/515.1 |
| 4,233,519 | 11/1980 | Coad | 250/515.1 |

Primary Examiner—Carolyn E. Fields
Assistant Examiner—John A. Miller
Attorney, Agent, or Firm—Barnes, Kisselle, Raisch, Choate, Whittemore & Hulbert

[57] ABSTRACT

A radiation field-shielding device is mounted on a collimator (4) in an radiotherapy apparatus. The collimator (4) is rotatable in a per se known manner about its axis and in its entirety about the horizontal axis of rotation of the radiotherapy apparatus for irradiating a patient lying on a treatment table. The device (5) comprises a housing (25) removably mounted on the collimator (4), and a holder (10) with radiation shield means (11) spaced from the collimator (4). The holder (10) is pivotable about a shaft (26) away from its position in front of the collimator (4) to a position at the side of the collimator (4), in which position the holder (10) is rotatable about a second shaft oriented towards the center of the holder (10) and extending at right angles to the first shaft (26). In this manner, there is obtained, by two simple operations of rotation, a mirror inversion of the shield means (11) without necessitating dismounting or shifting thereof. Rotation of the collimator (4) about its axis together with rotation of the rotary part (3) of the radiotherapy apparatus allows irradiation of the patient in opposite directions with the same shielding configuration.

16 Claims, 6 Drawing Sheets

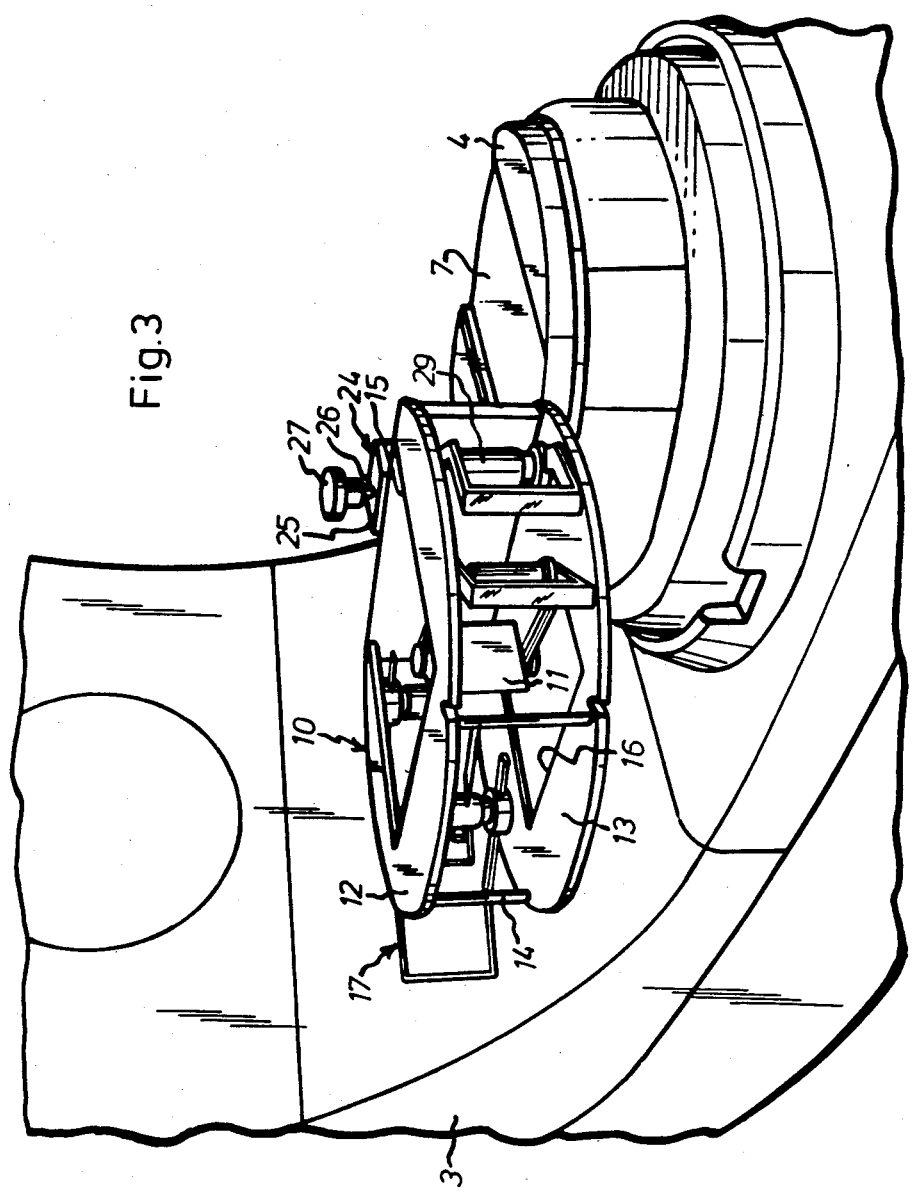

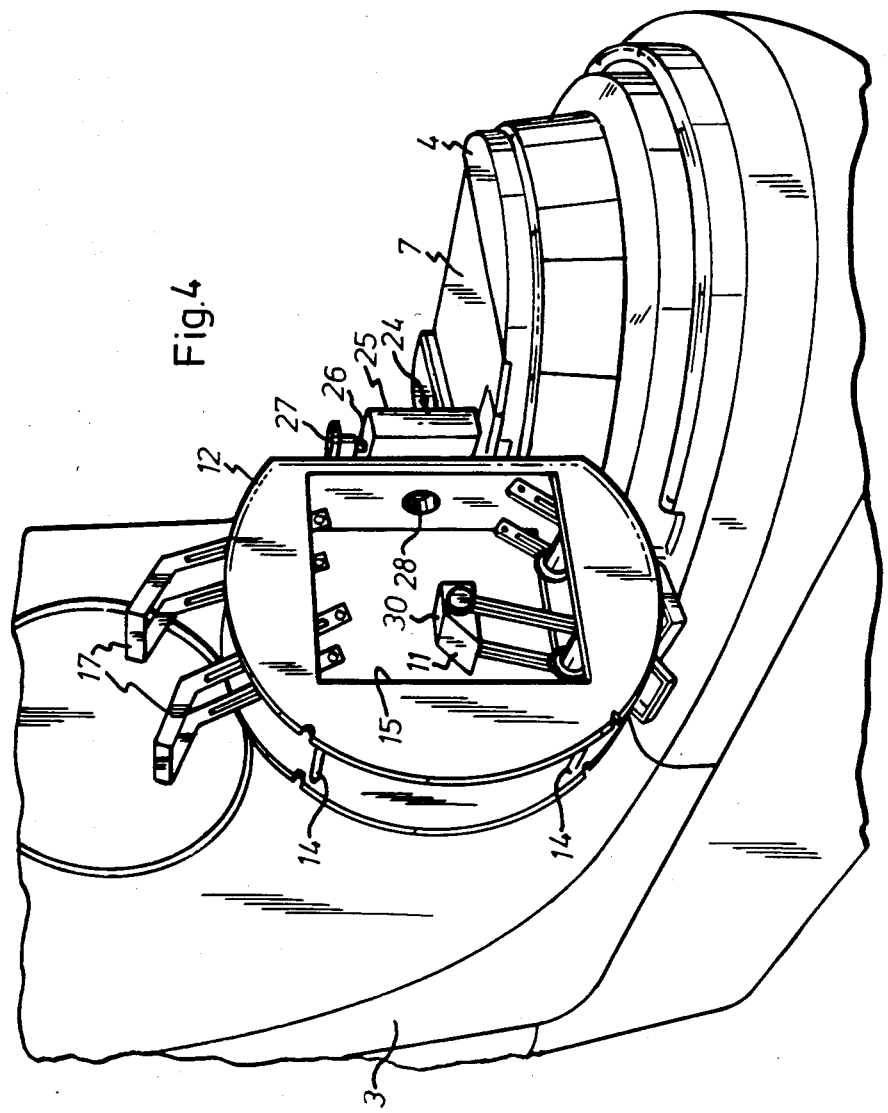

DEVICE FOR RADIATION FIELD SHIELDING IN RADIOTHERAPY

The present invention relates to radiation field shielding in a radiotherapy apparatus, and more particularly to a device for shielding the radiation field from a collimator unit which is included in the radiotherapy apparatus and which in a per se known manner is rotatable about its axis and rotatable in its entirety about an axis of rotation spaced from the collimator unit, such that this is rotatable about a patient to be subjected to radiation, the device being exchangeably mounted on the collimator unit and supporting in a holder at least one radiation shield means spaced from the collimator unit.

In radiotherapy, it is most essential that the patient be held in a correct position in relation to the radiotherapy apparatus. Also, very high demands are placed on the shielding of the radiation field from the collimator of the radiotherapy apparatus in order that radiation should be confined to the intended, clearly defined treatment area. Incomplete or incorrect radiation field shielding may cause damage to tissues outside the treatment area.

The collimator unit itself is generally provided with a so-called primary diaphragm for producing rectangular or square radiation fields. Often, it is however desired to have a shielding aperture of irregular shape, to which end use is made of a so-called satellite diaphragm in the form of a holder device which is mounted on the collimator and in which radiation shield means, such as lead blocks, are fixed for providing final shielding.

On the market, there are several different types of such holder devices having a similar basic design. One previously known holder device consists of a frame mounted on the collimator and supporting a slotted plexiglass plate spaced from the aperture of the collimator. Lead blocks, which can be fixed by different clamping means, are placed on or suspended from this plate. For example, the lead blocks have projecting threaded pins which are inserted through a slot in the plate, whereupon the blocks are fixed by screwing a wing nut on the pin and tightening it against the plate.

The known shielding and holder devices suffer from a number of drawbacks as regards both the handling of the lead blocks by the personnel and the radiotherapeutic treatment itself. First, the handling of the lead blocks involves heavy lifting since these blocks weigh up to about 20 kg. The personnel working at a radiotherapy apparatus may handle about 1000 kg lead during one working day, sometimes at an aergonomically very tiring height above the floor. Secondly, the blocks must be shifted when a certain part of the patient's body should be subjected to radiation from two directions and to a certain depth. The patient is in fact lying permanently fixed on the treatment table and if the patient after radiation in a first direction should be subjected to radiation in the opposite direction, the collimator is turned together with the shield device through 180° about the patient. The shield means are however then mirror-inverted and, thus, must be shifted in order to obtain the same desired orientation of the shield aperture as in connection with radiation in the first direction. Shifting the shield means is both physically tiring and time-consuming. Further, it is difficult to achieve high accuracy after mirror-inversion of the blocks since they must be dismounted and/or turned on the plexiglass plate.

The very fixing of the lead blocks is a problem since the blocks will easily loosen at oblique directions of radiation, i.e. when the axis of the collimator is oblique in relation to the vertical plane. If a lead block loosens during irradiation, this must be interrupted.

The apertured or slotted plexiglass plate is a problem itself since it gives an inhomogeneous radiation field. In the optimum case, no objects apart from the shield means must be in the zone between the aperture of the collimator and the part of the patient to be subjected to radiation.

One object of the present invention is to provide a device for supplementary shielding of the radiation field from a collimator unit included in a radiotherapy apparatus, which device readily allows irregular radiation field shielding in different, including opposite, directions without making it necessary to dismount or shift the shield means.

Another object is to provide such a shield device that reduces the frequency of heavy lifts and allows irradiation in all directions all the way around the patient without the shield means being moved from their shielding positions.

A further object of the invention is to provide a shield device which does not contain any image-impairing details in the radiation field.

Yet another object of the invention is to provide a shield device which can be mounted on existing radiotherapy apparatus without making it necessary to modify these in any way.

These and other objects which will appear from the following description are achieved in a most ingenious way by means of a shield device of the type described in the introduction to this specification, which is characterized by a shaft assembly which is mounted on the collimator unit and on which the holder is mounted at its periphery and which allows rotation of the holder about two shafts substantially at right angles to each other.

By means of the shield device of the invention, it is easy to effect mirror-inversion of the shield means, which makes it considerably easier to treat a patient who should be subjected to radiation in different directions. The shield means need not be shifted but constantly remain in the same position in the holder. This reduces the heavy handling of lead blocks required in prior art shield devices. Moreover, much greater accuracy is achieved since the lead blocks are not displaced from their positions. Another substantial advantage is that the shield device is exchangeable so that different shield devices can be used for different purposes. It may also be advantageous to use shield devices with certain "standard configurations" as regards the location and shape of the shield means.

The type of cassette often used when the area of the patient's body to be irradiated has an intricate shape may very well be used together with the shield device of the present invention. In this case, the holder has a suitable shape with respect to the cassette, but otherwise the function and the handling remain the same, as will be described in more detail hereinbelow.

The invention will be described in more detail in the following with reference to the accompanying drawings showing some embodiments of the invention.

FIG. 3 is a perspective view of the shield device with a holder for shield means located at the side of the collimator unit.

FIG. 4 shows the shield device in a position where the holder has been turned in relation to the collimator.

Figure 5A:
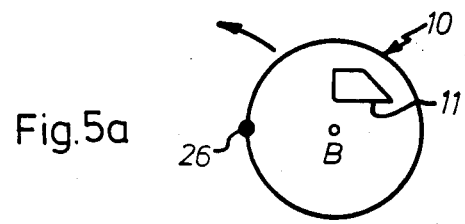
Figure 5B:
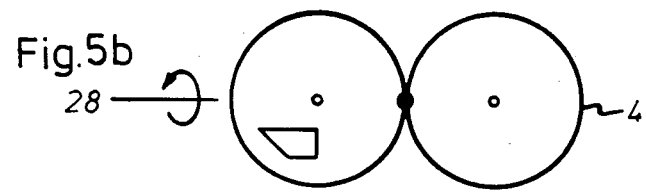
Figure 5C:
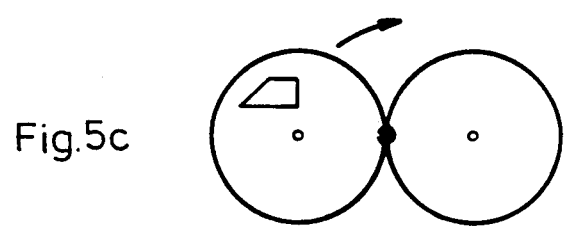
Figure 5D:
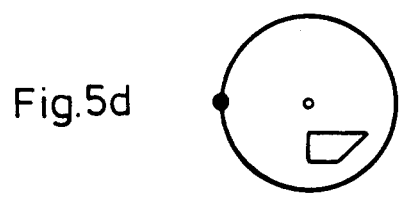
Figure 5E:
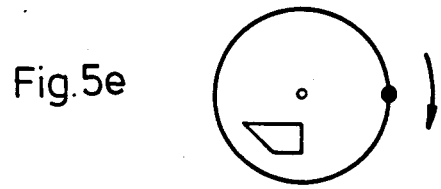
Figure 5F:
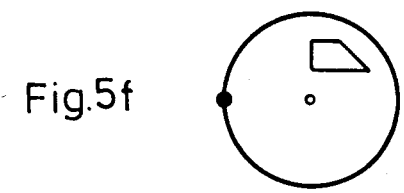

FIGS. 5a–5f schematically show different positions of the holder in which one shield means is mounted, FIG. 5a showing the position in the case of radiation from below, FIG. 5b showing the holder after rotation in a plane parallel to the plane of rotation of the collimator, FIG. 5c showing the holder after rotation in a plane at right angles to the plane of rotation of the collimator, FIG. 5d showing the holder in a retracted position, FIG. 5e showing the position after the collimator of the radiotherapy apparatus has been rotated through 180° about the patient for radiation from above, and FIG. 5c showing the position after the collimator and, thus, the shield device have been rotated about the axis of the collimator.

Figure 6:
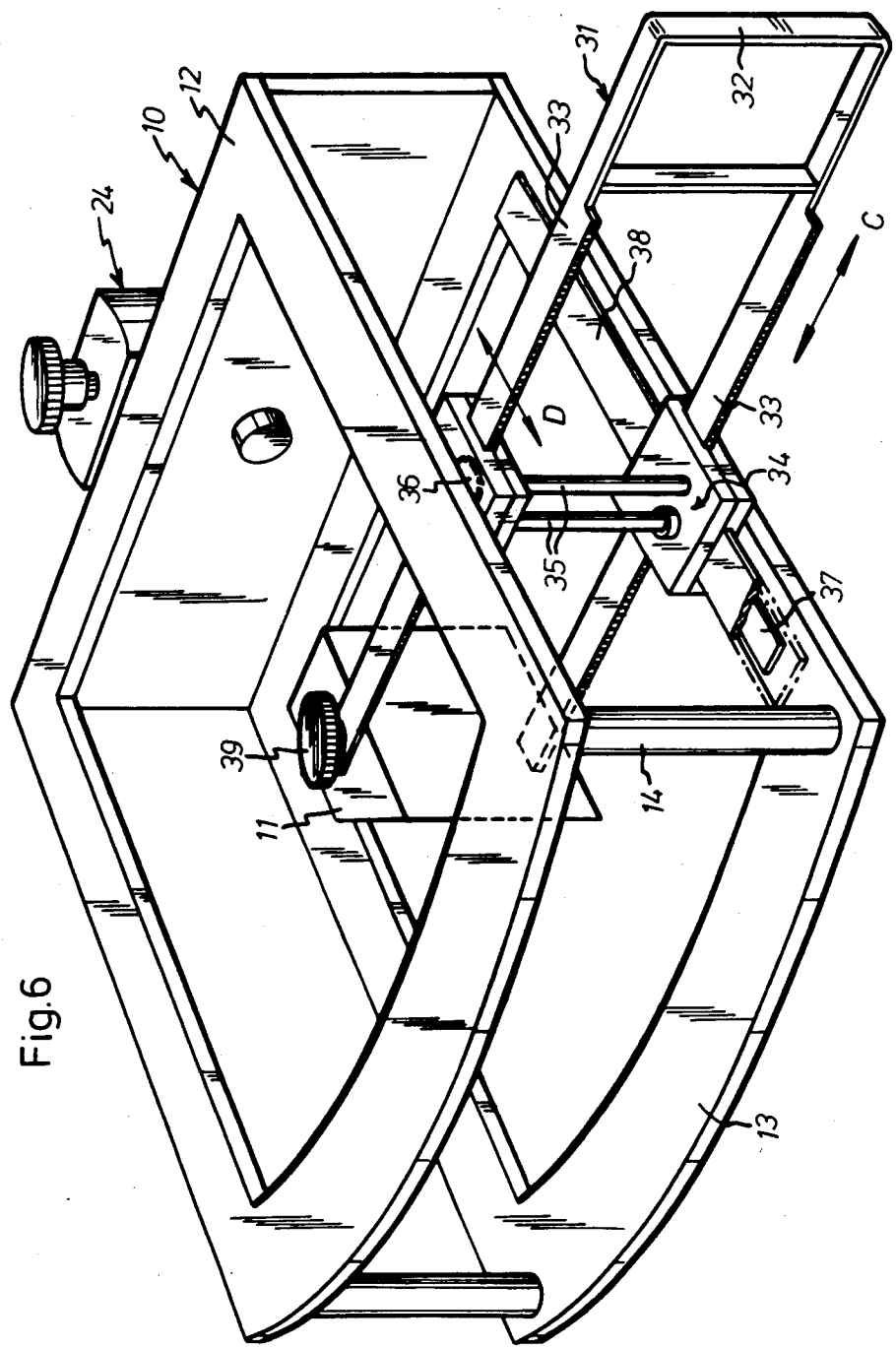

FIG. 6 shows an alternative holder for the shield means with certain parts removed.

Figure 1:
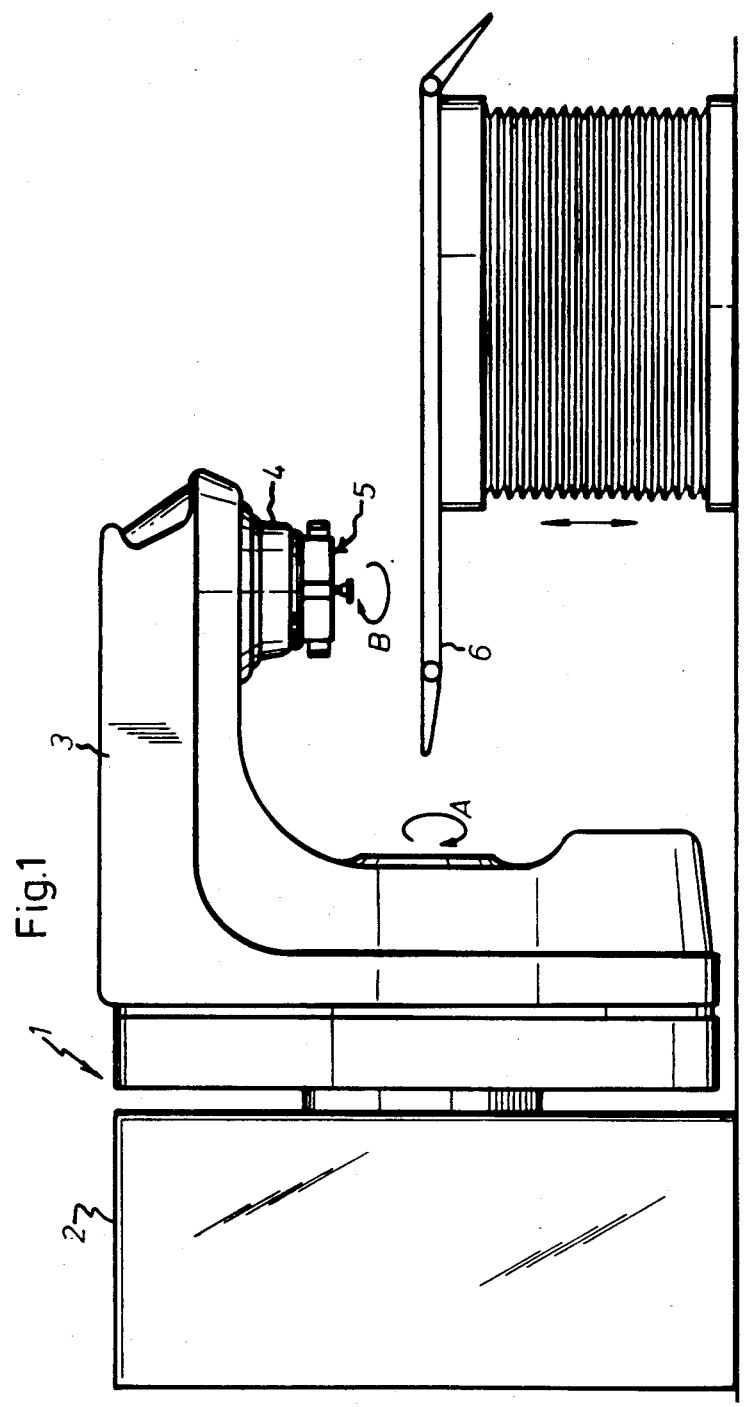
FIG. 1 is a side view showing a radiotherapy apparatus which has an inventive shield device and is disposed in association with a patient-supporting table for radiotherapy.

FIG. 1 shows an apparatus 1 for radiotherapy which in a per se known manner comprises a frame 2 standing on the floor and connected to an L-shaped rotary member 3 which is rotatable about a horizontal axis A. The horizontal portion of the rotary member 3 is provided with a collimator 4 on which a shield device 5 according to the invention is mounted. The collimator 4, and thus also the shield device 5, is rotatable about its axis B. Further, the horizontal portion of the rotary member 3, and thus also the collimator 4, is rotatable about a patient-supporting table 6 which preferably is vertically adjustable. In radiotherapy, an accurately positioned patient to be subjected to radiation, is lying on the table 6 and a radiation field from the collimator 4 is transmitted by the shield device 5 against the patient in different directions. In the position shown in FIG. 1, the patient should be irradiated from above, and rotation of the rotary member 3 through 180° about the axis A will allow radiation from below. Naturally, all directions of radiation all the way around the patient are possible.

Figure 2:
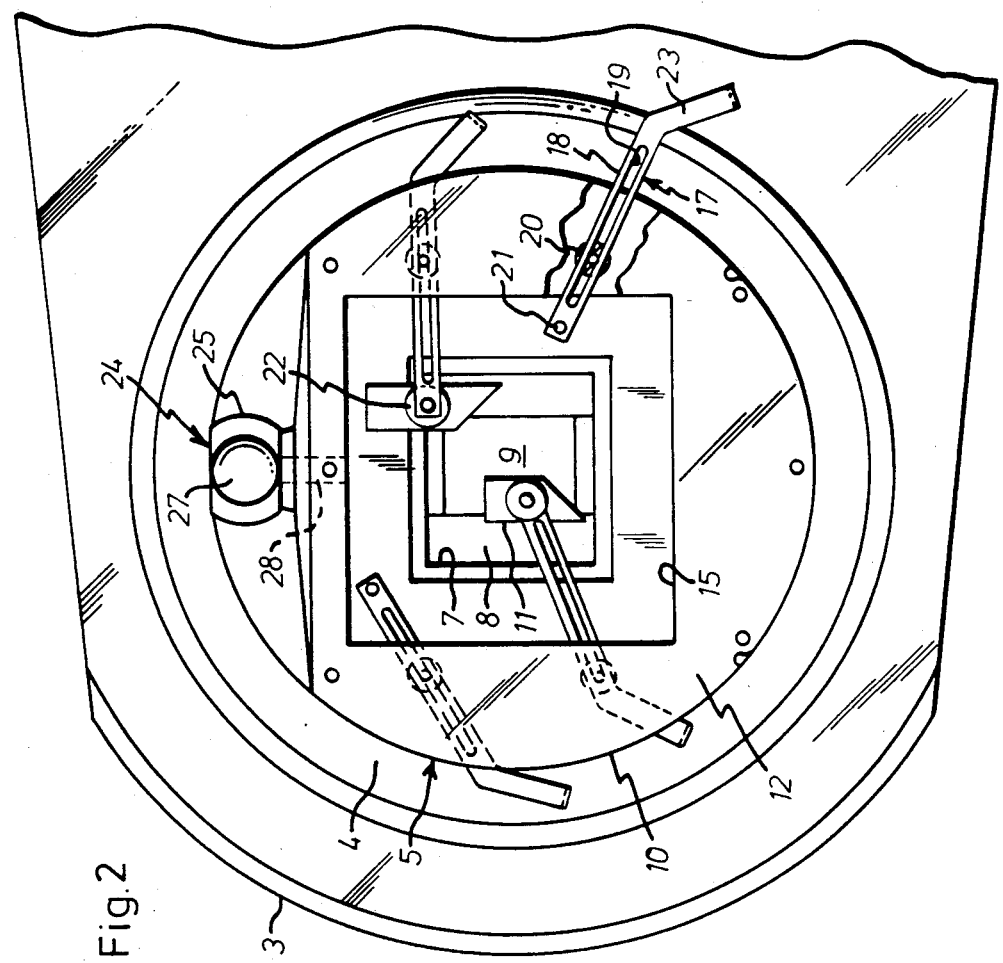
FIG. 2 shows the shield device mounted on a collimator as seen from in front and with certain parts removed.

FIG. 2 shows the shield device 5 mounted on the collimator 4 from in front. The collimator 4 has a collimator aperture 7 with four shield plates 8 which, according to known technique, are movable in pairs in the plane of the collimator aperture 7 so as to form a so-called primary diaphragm which normally provides rectangular or square radiation fields. In FIG. 2, the collimator plates 8 have been moved in such a manner that a rectangular radiation field 9 is formed.

The collimator 4 is equipped with a holder 10 for shield means 11 which in FIG. 2 are in the form of two lead blocks. The holder 10 consists of two parallel plates 12, 13 which are interconnected by means of a number of spacers 14 in the form of rods, as best seen in FIG. 3. The plates 12, 13 each have a central opening 15 and 16, respectively, correspondingly shaped and having such a size as to allow free passage of a maximum radiation field from the collimator aperture 7. For supporting shield means 11, four operating arms 17 are mounted in the holder 10 for providing a so-called satellite diaphragm, i.e. a diaphragm having a shield aperture in which the radiation field 9 is shielded outside the collimator aperture 7. Each operating arm 17 has two shanks 18 extending towards the centre of the holder 10 and having a longitudinal slot 19 into which a post 20 fixedly mounted in the holder 10 extends at right angles to the shank 18. Each shank 18 has at its proximal end with respect to the centre of the holder 10 a hole 21 for mounting a shield means 11 with the aid of a rotatable clamping element 22. At their distal ends with respect to the centre of the holder 10, the shanks 18 are connected to each other so as to form a handle 23. For positioning the shield means 11, the user actuates the handle 23 by linearly moving the operating arm 17 along the slots 19 and/or by pivoting the operating arm 17 about the post 20. In this manner, the shield means 11 can be brought into any desired position in front of the collimator aperture 7. The adjustment of the shield means 11 is easily achieved since it is pivotally mounted between the shanks 18 and accessible by the free opening 15, 16 of the holder, as are the clamping elements 22.

As further appears from FIG. 2, the holder 10 is mounted on the collimator 4 at its periphery by means of a shaft assembly 24 consisting of a housing 25 and two shafts which are at right angles to each other and which will be described in more detail hereinbelow. The holder 10 is pivotal about a first shaft 26 (see FIG. 3) extending through the housing 25 at right angles to the plane of rotation of the collimator 4 and parallel to the axis B of the collimator 4. One end portion of the first shaft 26 engages in a recess (not shown) at the periphery of the collimator 4, while its other end portion is provided with a knob 27 by means of which the holder 10 can be clamped in different positions. If so desired, the holder 10 can be removed from the collimator 4 by loosening the knob 27 and removing the holder 10.

A second shaft 28 (indicated by dashed lines in FIG. 2) which projects from the housing 25 is perpendicular to the first shaft 26 and extends inwards towards the centre of the holder 10. After the holder 10 has been swung away from its position in front of the collimator 4, it can be rotated about its second shaft 28, as best seen in FIGS. 3 and 4. During radiation, the holder 10 is accurately fixed in relation to the collimator 4 by means of a clamping device not shown or described in more detail, which engages the periphery of the holder 10. In this position, the second shaft 28 is directed towards the axis B of the collimator 4.

In FIG. 3, the rotary member 3 of the radiotherapy apparatus 1 is shown in a position corresponding to a rotation thereof through 180° about the axis of rotation A, as compared with FIG. 1. The holder 10 is shown in a position swung out from the collimator unit 4, where the position of the shield means 11 can be adjusted by means of the operating arms 17 (only one shield means 11 is shown in FIG. 3). After completed adjustment, each operating arm 17 can be fixed further by means of a double-acting clamping element 29 disposed around the above-mentioned post 20 and consisting of locking devices which are mounted in pairs and which are individually and symmetrically fixed on the respective plate 12, 13 and the simultaneous operation of which is in principle analogous with that of a turnbuckle, however without affecting the distance between the plates 12, 13. In the position shown in FIG. 3, the holder 10 is at a height above the floor which is convenient to the personnel and, thus, the above-mentioned adjusting operations are very readily performed and require but a small physical effort. The above-debated heavy lifts and shifting of the shield means 11 which are often carried out at a considerable height above the floor (see FIG. 1) can thus be avoided. If so desired, it is possible to remove the holder 10 from the collimator 4 and place it on a table beside the radiotherapy apparatus and instead perform the adjusting operations with the holder 10 on the table. It is then possible to simulate the radiation field by illuminating the holder 10 placed on the table from above, and adjust the desired shielding effect of the shield means 11 by operating the arms 17. In this case, the table is preferably provided with a cloth on which the shadow image is sharply outlined against a contour image of the desired field shape.

In FIG. 4, it is shown how the holder 10 is rotatable about the second shaft 28 of the housing 25. The holder 10 is rotated through 90° as compared with the position shown in FIG. 3. If further rotated through 90°, the shield means 11 will assume a mirror-inverted position as compared with FIG. 3 and with respect to the second shaft 28. If the holder 10 is pivoted about the first shaft 26 back to the position in front of the collimator 4, mirror-inverted shielding is thus obtained, as will be described in more detail hereinbelow.

The use of the shield device 5 according to the invention clearly appears from a functional description with reference to FIGS. 5a-5f illustrating the operational steps in a radiotherapeutic treatment in two directions, i.e. from above (FIG. 1) and from below (rotary member 3 rotated through 180° in relation to FIG. 1). First, the patient is irradiated from below, see FIG. 5a, the shield means 11 mounted in the holder 10 being in a first position. When this first step has been terminated, the knob 27 is loosened and the holder 10 is swung through 180° about the first shaft 26 to the position shown in FIG. 5b, corresponding to FIG. 3. The holder 10 is thereafter rotated through 180° about the second shaft 28, as schematically shown in FIG. 5b, and again pivoted about the first shaft 26 back to the initial position in front of the collimator 4, see FIGS. 5c and 5d. In this position, the shield means 11 is mirror-inverted with respect to the second shaft 28, which is now oriented towards the axis B of the collimator 4. The rotary member 3 of the radiotherapy apparatus 1 is thereafter rotated through 180° about the axis of rotation A so as to occupy the position shown in FIG. 1. The holder 10 thus is in the position shown in FIG. 5e. Finally, the collimator 4 is rotated through 180° about its axis B to the position shown in FIG. 5f, in which the shield means 11 is in correct shielding position and radiation from above can be initiated. Mirror inversion of the shield means 11 is thus brought about in a very simple manner by the above-described rotation of the holder 10 about the second shaft 28 at the side of the collimator 4.

For achieving optimum results in radiotherapy as described above with mirror inversion of the shield means 11, preferably consisting of lead blocks or the like, the sides 30 of the shield means 11 parallel to the axis B of the collimator 4 are double-chamfered for adaptation to the divergent radiation field of the collimator 4. Otherwise, mirror inversion may give rise to different radiation areas on the patient when irradiated in different directions.

FIG. 6 shows a variant of the holder 10 having another type of operating arm 31 comprising a handle 32 and two parallel shanks 33 in the form of racks which extend inwards towards to the centre of the holder 10 and are movable in the direction of an arrow C by means of a shaft-gear wheel assembly 34 which includes inter alia two similar shafts 35 and gear wheels 36 (only one of the four gear wheels is shown) fixed at the ends of the shafts 35. The operating arm 31 is also movable in its entirety in the direction of an arrow D in that the holder 10 includes two fixedly mounted racks 37 (of which only one is shown) for meshing with both gear wheels 36 of one shaft 35. Over each rack 37 there is placed a guide rail 38 for guiding the movement along the rack 37. Thus, the operating arm 31 is movable in its longitudinal direction through the shaft-gear wheel assembly 34 which in turn is movable transversely of said direction. The racks 33 and 37 may be regarded as guides for the operating arm 31.

A shield means 11 is fixed at the ends of the two racks 33 by means of a clamping element 39 of the type described above. It is evident to the skilled reader how the shield means 11, by means of the abovedescribed arrangement, is movable in two directions C and D at right angles to each other for optional adjustment of the shield means 11 in the holder 10. As before, the shield means 11 can of course be turned for still more accurate shielding. Although, for reasons of clarity, only one operating arm 31 is shown, it is understood that several arms may be used. In a preferred embodiment of the invention, the holder 10 is provided with four operating arms 31, two on each side of the holder 10.

A tested method in radiotherapy is placing a cassette (not shown) in a holder in front of the collimator. The cassette is produced on the basis of an X-ray picture showing the zone to be irradiated. The shape of this zone is cut out in a piece of material which is easy to work, such as Frigolit ®, and the cut-out space is filled with a metal having a low melting point and relatively high density, such as Wood's metal. It is also possible to use lead shots of different diameter. Thus, the metal will serve as shield means. The cassette consisting of frigolit and metal is inserted in a holder in front of the collimator and radiotherapy is effected in the manner described above. Provided the piece of metal used in the cassette has a double-divergent shape, this cassette technique may be used to advantage together with a shield device according to the invention. The mirror-inversion principle relying on the shaft assembly 24 with the mutually perpendicular shafts 26 and 28 is then equally useful. It is also conceivable to insert cassettes in the holder 10 described above. In such a case, the operating arms 17 or 31 are removed from the opening 15, 16 of the holder 10 and the cassette is placed between the plates 12, 13 and fixed by means of any suitable type of clamping device.

To check that correct cassettes are used, a code system (not shown) is advantageously used having multipolar contacts on the holder and on the different cassettes. When a certain cassette should be used, it is inserted in the holder and the contacts are engaged with each other. A preset code on the contacts of the holder should then agree with the code on the contacts of the cassette. If the codes do not agree, the current supply is interrupted and irradiation with the incorrect cassette is not feasible. In this manner, the code system ensures that the patient is subjected to radiation with the correct cassette.

For reasons of clarity, the holder 10 is shown in FIGS. 1-4 directly mounted on the collimator 4. However, use is advantageously made of a spacer plate (not shown) which is fixed on the collimator 4 and has recesses and fixing means for safely mounting the holder 10. It is evident that substantial advantages are gained by the possibility of using different spacer plates adapted to radiotherapy apparatus of different designs, while using the same holder 10.

Finally, it should be mentioned that the shield device according to the invention is also usable in connection with recently developed primary diaphragms allowing asymmetric adjustment of one pair of shield plates for producing very complicated radiation fields. It is only for reasons of simplicity that the embodiment here described uses a collimator 4 having four collimator plates 8 symmetrically movable in pairs.

I claim:

1. A device for shielding the field of radiation in a radiotherapy apparatus (1) comprising a frame (2) and a rotary member (3) rotatable about a first axis (A) and a collimator unit (4) having a second axis (B) which is rotatable in its entirety about said first axis (A) spaced apart from said collimator unit (4), such that the collimator unit is rotatable about a patient to be subjected to radiation, said device (5) being mounted on the collimator unit (4) and comprising a holder (10) which supports at least one adjustable radiation shield means (11) spaced from the collimator unit (4), said device (5) having a shaft assembly (24) which is mounted on the collimator unit (4) and on which the holder (10) is mounted, characterized in that the shaft assembly (24) comprises two shafts (26, 28) having axes substantially at right angles to each other, the holder (10) being pivotable about one (26) of said shafts from a first position in front of the collimator unit (4), such that radiation passing through the collimator unit passes through an opening in the holder, to a second position in which the holder (10) is pivoted away from the collimator unit (4) and in which the holder is rotatable in its entirety about the axis of the other shaft (28).

2. Device as claimed in claim 1, characterized in that it is exchangeably mounted on the collimator unit (4) and that the shaft assembly (24) comprises a housing (25) which is removably mounted at the periphery of the collimator unit (4) and in which said two shafts (26, 28) are fixedly mounted.

3. Device as claimed in claim 1, characterized in that the holder (10) has operating means (17; 31) for positioning the radiation shield means (11) in a central opening (15, 16) in the holder (10).

4. Device as claimed in claim 3, characterized in that the operating means comprises an arm (17; 31) at one end of which the shield means (11) is rotatably and exchangeably mounted and the other end of which consists of a handle (23; 32), the operation of the handle bringing about said positioning of the shield means (11).

5. Device as claimed in claim 4, characterized in that the arm (17) comprises two shanks (18) which project from the handle (23) and between the end portions of which said shield means (11) is mounted, that each shank (18) has an elongated slot (19) into which a post (20) fixedly mounted in the holder (10) extends substantially at right angles to the shank (18), and that the positioning of the shield means (11) is brought about by linear displacement of the arm (17), said displacement being guided and restricted by means of the slots (19) of the shanks (18), and/or by rotation of the arm (17) about the post (20).

6. Device as claimed in claim 5, characterized in that a double-acting clamping means (29) is provided in association with each post (20) for fixing the position of the shield means (11).

7. Device as claimed in claim 4, characterized in that the arm (31) is movable in two directions (C, D) at right angles to each other by means of two guides (33, 37) at right angles to each other, for optional positioning of the shield means (11).

8. Device as claimed in claim 7, characterized in that said guides comprise four racks (33, 37) the first two of which are two parallel spacedapart shanks (33) forming the arm (31) and displaceably mounted in a shaft-gear wheel assembly (34) for moving the arm (31) in the longitudinal direction (C) thereof, while the other two (37) are parallel and fixedly mounted on the holder (10) in spaced-apart relationship, said shaft-gear wheel assembly (34) and the arm (31) mounted therein being movable together along the fixed racks (37) in said other direction (D), and all of said racks (33, 37) meshing with gear wheels (36) included in said assembly (34).

9. Device as claimed in any one of claims 1-8, characterized in that each shield means is a block (11) whose sides (30) substantially parallel to the axis (B) of the collimator unit (4) are doublechamfered for adaptation to the divergent radiation fields of the collimator unit (4).

10. Device as claimed in claim 2, characterized in that the holder (10) has operating means (17; 31) for positioning the radiation shield means (11) in a central opening (15, 16) in the holder (10).

11. Device as claimed in claim 10, characterized in that the operating means comprises an arm (17; 31) at one end of which the shield means (11) is rotatably and exchangeably mounted and the other end of which consists of a handle (23; 32), the operation of the handle bringing about said positioning of the shield means (11).

12. Device as claimed in claim 11, characterized in that the arm (17) comprises two shanks (18) which project from the handle (23) and between the end portions of which said shield means (11) is mounted, that each shank (18) has an elongated slot (19) into which a post (20) fixedly mounted in the holder (10) extends substantially at right angles to the shank (18), and that the positioning of the shield means (11) is brought about by linear displacement of the arm (17), said displacement being guided and restricted by means of the slots (19) of the shanks (18), and/or by rotation of the arm (17) about the post (20).

13. Device as claimed in claim 12, characterized in that a double-acting clamping means (29) is provided in association with each post (20) for fixing the position of the shield means (11).

14. Device as claimed in claim 11, characterized in that the arm (31) is movable in two directions (C, D) at right angles to each other by means of two guides (33, 37) at right angles to each other, for optional positioning of the shield means (11).

15. Device as claimed in claim 14, characterized in that said guides comprise four racks (33, 37) the first two of which are two parallel spaced-apart shanks (33) forming the arm (31) and displaceably mounted in a shaft-gear wheel assembly (34) for moving the arm (31) in the longitudinal direction (C) thereof, while the other two (37) are parallel and fixedly mounted on the holder (10) in a spaced-apart relationship, said shaft-gear wheel assembly (34) and the arm (31) mounted therein being movable together along the fixed racks (37) in the other direction (D), and all of said racks (33, 37) meshing with gear wheels (36) included in said assembly (34).

16. Device as claimed in any one of claims 1, 2 or 10-15, characterized in that the shield means (110) comprise a cassette provided with shielding blocks and fixable in the holder (10) independently of other fixing and operating means.

* * * * *